(12) United States Patent
Ookubo

(10) Patent No.: US 7,651,861 B2  
(45) Date of Patent: Jan. 26, 2010

(54) METHOD OF PRODUCING FLUORITE CRYSTAL, FLUORITE AND OPTICAL SYSTEM INCORPORATING THE SAME

(75) Inventor: Kenji Ookubo, Atsugi (JP)

(73) Assignee: Canon Kabushiki Kaisha, Tokyo (JP)

( * ) Notice: Subject to any disclaimer, the term of this patent is extended or adjusted under 35 U.S.C. 154(b) by 686 days.

(21) Appl. No.: 11/358,103

(22) Filed: Feb. 22, 2006

(65) Prior Publication Data

US 2006/0153263 A1    Jul. 13, 2006

Related U.S. Application Data

(62) Division of application No. 10/187,799, filed on Jul. 3, 2002, now Pat. No. 7,035,306.

(30) Foreign Application Priority Data

Jul. 5, 2001    (JP) ............... 2001/205469

(51) Int. Cl.
    *G01N 33/00*    (2006.01)
(52) U.S. Cl. ............... 436/124; 501/86; 117/11
(58) Field of Classification Search ........... 436/124; 501/86; 117/11
    See application file for complete search history.

(56) References Cited

U.S. PATENT DOCUMENTS

| | | | |
|---|---|---|---|
| 4,740,982 A | 4/1988 | Hakuta et al. | 372/59 |
| 6,028,880 A | 2/2000 | Carlesi et al. | 372/58 |
| 6,240,117 B1 | 5/2001 | Gong et al. | 372/58 |
| 6,804,285 B2 | 10/2004 | Ohmi et al. | 372/58 |
| 6,878,201 B2 | 4/2005 | Oba et al. | 117/76 |
| 6,930,837 B2 | 8/2005 | Shafer et al. | 359/649 |

FOREIGN PATENT DOCUMENTS

| | | |
|---|---|---|
| EP | 0 869 203 A2 | 10/1998 |
| EP | 0 995 820 A2 | 4/2000 |
| EP | 1 037 267 A1 | 9/2000 |
| JP | 2000-119097 | 4/2000 |

OTHER PUBLICATIONS

J.T. Mouchovski et al., "Growth of Ultra-Violet Grade CaF2 Crystals and Their Application for Excimer Laser Optics," 162 *J. Cryst. Growth* 79-82 (1996).

Aierken Sidike et al., "Photoluminescence Properties of a Natural Fluorite," 95 *J. Menral. Petrol. Sci.* 228-35 (2000).

*Primary Examiner*—Yelena G Gakh  
*Assistant Examiner*—David Weisz  
(74) *Attorney, Agent, or Firm*—Fitzpatrick, Cella, Harper & Scinto (57) ABSTRACT

There is provided a method of forming a fluorite crystal and an exposure apparatus including this fluorite crystal. A method of manufacturing a device using the exposure apparatus is also provided.

1 Claim, 6 Drawing Sheets

METHOD OF PRODUCING FLUORITE CRYSTAL, FLUORITE AND OPTICAL SYSTEM INCORPORATING THE SAME

This Application is a division of application Ser. No. 10/187,799, filed Jul. 3, 2002, now U.S. Pat. No. 7,035,306 B2, which is incorporated herein by reference.

FIELD OF THE INVENTION AND RELATED ART

This invention relates to a fluorite crystal to be used as an optical element in a photolithographic apparatus, which uses, for example, an excimer laser to generate exposure light, as well as to an assaying method, a production method and optical characteristics evaluation method for such a fluorite crystal. In another aspect, the invention concerns an optical system using a fluorite crystal, an exposure apparatus using such an optical system, and a device manufacturing method using such an exposure apparatus.

In order to meet recent notable advancement in miniaturization of semiconductor circuits, the wavelengths of light sources used in semiconductor exposure apparatuses have been reduced. Currently, exposure apparatuses using the $F_2$ excimer laser ($\lambda$: 157 nm) are being widely developed. Under these circumstances, fluorite is expected to be an effective optical material that ensures good durability and transmissivity of short wavelengths.

However, when the fluorite contains impurities, its durability and transmissivity will decrease. Since this effect becomes more pronounced as the wavelength of light source becomes shorter, the impurity content is, in fact, a serious problem when fluorite is to be used as an optical material in an exposure apparatus.

In order to solve this problem, there have been attempts to improve the purity of fluorite. At present, except for congeners of Ca, such as Mg, Sr and Ba, fluorite crystals having such a purity level that no impurity can be observed in accordance with conventional assaying methods, are obtained. A typical example of a conventional assaying method is a procedure in which a fluorite sample is dissolved with an acid into a solution, which is then assayed on the basis of ICP-MS/ICP-OES (Inductively Coupled Plasma-Optical Emission Spectrometry). With such conventional methods, the impurity content in fluorite can be assayed quantitatively to a concentration level on the order of a few ppb.

It should be noted, however, that even such a high-purity fluorite does not assure sufficient durability and transmissivity with respect to ArF excimer lasers ($\lambda$: 193 nm) or $F_2$ excimer lasers. Therefore, the problem with the level of purity still remains.

Namely, fluorite crystals of a purity higher than what is obtainable currently are required. However, it is extremely difficult to meet this requirement, because most impurities in fluorite are not observed using conventional assay methods. On the one hand, a quantitative method for effectively reducing what is invisible is difficult to accomplish. On the other hand, contamination during the manufacturing process cannot be identified. It is not known which element is undesirable in connection with the optical characteristics, to what level such an element should be reduced and, more fundamentally, whether a further reduction of impurities has a real significance in improving optical characteristics, etc. Where impurities are at a slight trace level, on the order of a few ppb or lower, it may be hypothesized that a factor other than the impurities, such as the level of crystallinity, is largely responsible for the deterioration of optical characteristics. Thus, the absence of particular guidelines fetters the development of high-quality fluorite having good optical characteristics.

SUMMARY OF THE INVENTION

In order to overcome these problems, it is an object of the present invention to provide a fluorite assaying method that is several times more sensitive than conventional methods.

It is another object of the present invention to provide fluorite, which satisfies an impurity concentration range determined as being ideal for optical characteristics on the basis of the results of the assay.

It is a further object of the present invention to provide a method of producing fluorite for satisfying the allowable impurity concentration range.

It is yet a further object of the present invention to provide an optical characteristic evaluation method, which is based on an impurity assay for a fluorite crystal.

It is yet a further object of the present invention to provide an optical system using such a fluorite crystal, a semiconductor manufacturing exposure apparatus using such an optical system, and/or a device manufacturing method based on such a semiconductor exposure apparatus.

Particularly, in conventional optical characteristics evaluation methods, a sample is polished with a high precision and the characteristics of the same are measured while ArF or $F_2$ excimer laser light is projected thereto for a long period of time. Such an evaluation method, therefore, is complicated, requires a lengthy amount of time and is expensive. Therefore, there is indeed a large problem with respect to the optical characteristics evaluation, and a simple evaluation method to be substituted for conventional methods is desired.

In accordance with an aspect of the present invention, there is provided an assaying method for a fluorite sample, the method comprising: a first step of dissolving a fluorite sample, containing Ca and F, by use of a solvent; a second step of removing Ca and F from an obtained solution; and a third step of assaying, through ICP-MS, the solution from which Ca and F have been removed.

In one preferred form of this aspect of the present invention, the first step comprises a procedure of transforming the fluorite sample into a calcium nitrate solution by use of nitric acid. The second step comprises a procedure in which the calcium nitrate solution is kept hot to remove the solvent, to thereby remove HF and excess nitric acid produced in the calcium nitrate solution, in which a residual solute being dissolved into an aqueous solution is then passed through an imino diacetate-type chelating resin at an appropriate pH to separate and remove Ca, and in which an element absorbed into the imino diacetate-type chelating resin is extracted by using nitric acid.

In accordance with another aspect of the present invention, there is provided an exposure apparatus having one of an ArF excimer laser and an $F_2$ excimer laser as a light source, characterized in that all lens elements used in an illumination optical system and a projection optical system of this exposure apparatus contain calcium fluoride as a major component and also contain not greater than 3 ppb of each of the following fifteen elements: Y, La, Ce, Pr, Nd, Sm, Eu, Gd, Tb, Dy, Ho, Er, Tm, Yb and Lu.

In accordance with a further aspect of the present invention, there is provided a method of producing a fluorite crystal, comprising: a first step of fusing a fluorite raw material having a scavenger added thereto to provide a refined product; a second step of fusing and re-crystallizing the refined product to provide an ingot; a third step of annealing the obtained ingot at a temperature not greater than a melting point, thereby improving crystallinity and providing an annealed product; a fourth step of performing a quantitative assay of at least one of fifteen elements (Y, La, Ce, Pr, Nd, Sm, Eu, Gd, Tb, Dy, Ho, Er, Tm, Yb and Lu) with respect to at least one of the fluorite raw material, the refined product, the ingot and the annealed product; and a fifth step of controlling the first, second and third steps on the basis of the result of the assay.

The fourth step may comprise a procedure for performing a quantitative assay as to all the fifteen elements (Y, La, Ce, Pr, Nd, Sm, Eu, Gd, Tb, Dy, Ho, Er, Tm, Yb and Lu) with respect to at least one of the fluorite raw material, the refined product, the ingot and the annealed product.

An average weight rate of each of Y, La, Ce, Pr, Nd, Sm, Eu, Gd, Tb, Dy, Ho, Er, Tm, Yb and Lu may not be greater than 100 ppb.

An average weight rate of each of Y, La, Ce, Pr, Nd, Sm, Eu, Gd, Tb, Dy, Ho, Er, Tm, Yb and Lu in the refined product may not be greater than 80 ppb.

An average weight rate of each of Y, La, Ce, Pr, Nd, Sm, Eu, Gd, Tb, Dy, Ho, Er, Tm, Yb and Lu in the ingot may not be greater than 50 ppb.

An average weight rate of each of Y, La, Ce, Pr, Nd, Sm, Eu, Gd, Tb, Dy, Ho, Er, Tm, Yb and Lu in the annealed product may not be greater than 50 ppb.

In accordance with yet another aspect of the present invention, there is provided a fluorite produced in accordance with at least one of the fluorite crystal producing methods as recited above.

In accordance with a further aspect of the present invention, there is provided an optical system for use with ultraviolet light as a light source, characterized in that the fluorite as recited above is used therein.

In accordance with yet another aspect of the present invention, there is provided an exposure apparatus, characterized in that an optical system as recited above is used therein.

In accordance with a further aspect of the present invention, there is provided a device manufacturing method, characterized in that an exposure apparatus as recited above is used in an exposure step for the device manufacture.

In accordance with another aspect of the present invention, there is provided a method of evaluating an optical characteristic of a fluorite, characterized in that a quantitative assay is performed with respect to at least one of the following element in the fluorite: Y, La, Ce, Pr, Nd, Sm, Eu, Gd, Tb, Dy, Ho, Er, Tm, Yb and Lu.

The quantitative assay may be based on an ICP-MS assay method.

The quantitative assay may be based on a laser abrasion ICP-MS assay method.

In accordance with yet another aspect of the present invention, there is provided a fluorite, characterized in that at least one of the optical characteristic evaluating methods as recited above is applied.

In accordance with a further aspect of the present invention, there is provided an optical system for use with ultraviolet light as a light source, characterized in that a fluorite as recited above is used therein.

In accordance with a further aspect of the present invention, there is provided an exposure apparatus, characterized in that an optical system as recited above is used therein.

In accordance with yet another aspect of the present invention, there is provided a device manufacturing method, characterized in that an exposure apparatus as recited above is used in an exposure step for the device manufacture.

In order to solve the problems encountered before the instant invention, the present invention provides a sample pre-processing method, which includes dissolution of a fluorite sample, removal of a matrix (such as Ca, F, and solvent used for dissolution, for example), and a concentration process for residual impurity elements, as well as an assay method, which is characterized by the use of ICP-MS (Inductively Coupled Plasma-Mass Spectrometry Apparatus). With these methods, a limit of quantitative determination of 0.1 ppb, which means that the sensitivity is a hundred times greater than that of conventional methods, can be attained. This is the highest sensitivity for fluorite, compared to any assay results published up to the present date.

In a fluorite assay method, as a sample pre-processing procedure, the fluorite sample may be transformed into a calcium nitrate solution by use of nitric acid, and the calcium nitrate solution may be kept hot to remove the solvent, thereby removing HF and excessive nitric acid produced in the calcium nitrate solution. A residual solute dissolved into an aqueous solution may then be passed through an imino diacetate-type chelating resin at an appropriate pH to separate, by absorption, primarily, metal elements and rare earth elements. The element absorbed into the imino diacetate-type chelating resin may be extracted using nitric acid. With this procedure, removal of a matrix (such as Ca, F and nitric acid used for the dissolution), as well as a concentration of contained impurity elements, can be accomplished. This assay method is effective mainly with respect to metal elements and rare earth elements, as a high-sensitivity assay, and a limit of quantitative determination of 0.1 ppb can be attained.

Figure 1A:
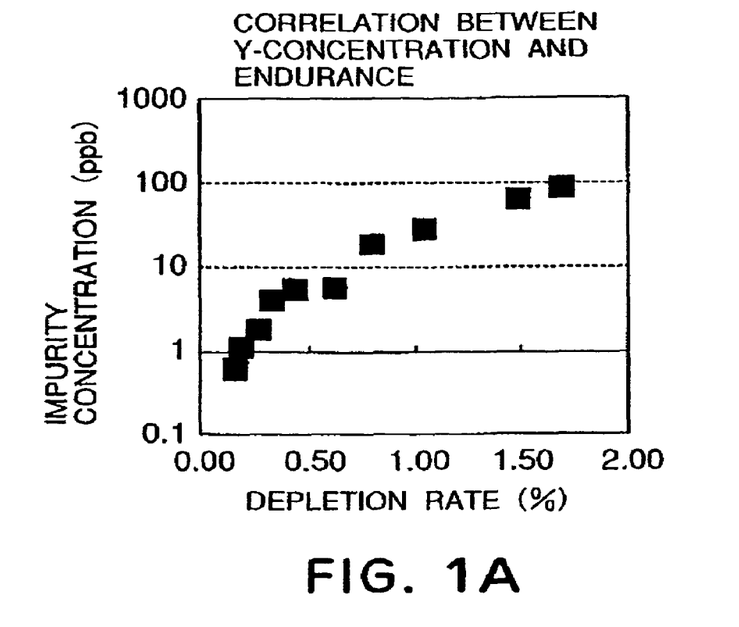
FIGS. 1A and 1B are graphs, respectively, for explaining correlations of durability and transmissivity to Y concentration in fluorite and an ArF excimer laser light.
Figure 1B:
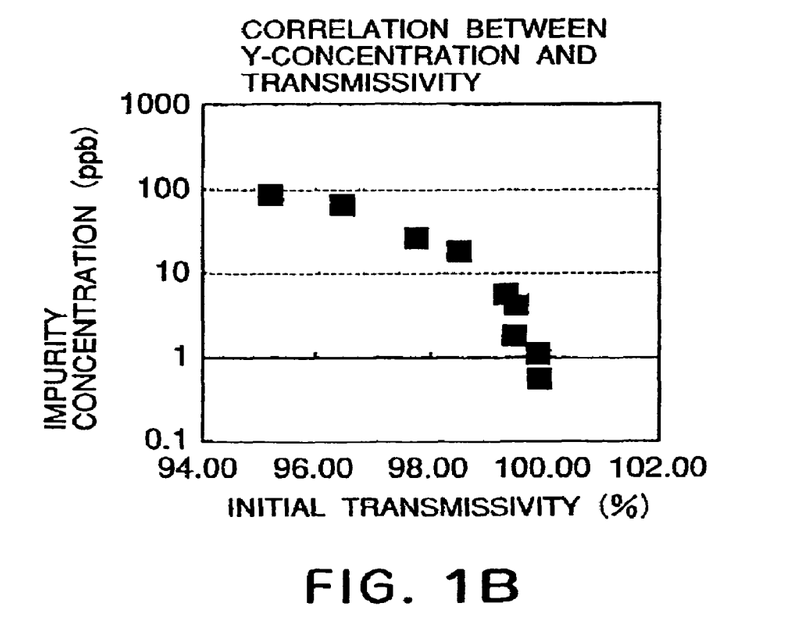

The inventor has measured an impurity content in fluorite in accordance with this newly established assay method and at a sensitivity of a quantitative determination limit of 0.1 ppb. Also, the inventor investigated in detail the correlation between the impurity content and the durability and transmissivity of fluorite. It has been confirmed experimentally that there is a correlation between rare earth elements and the optical characteristic of fluorite, such as depicted in FIGS. 1A and 1B. Since the durability to an $F_2$ excimer laser light exposure corresponds approximately to that obtainable by multiplying the depletion rate (deterioration level) with respect to ArF by about 1.5, and the transmissivity corresponds to that obtainable by multiplying the value with respect to ArF by about 0.99, they are not illustrated in the drawings.

Figure 2:
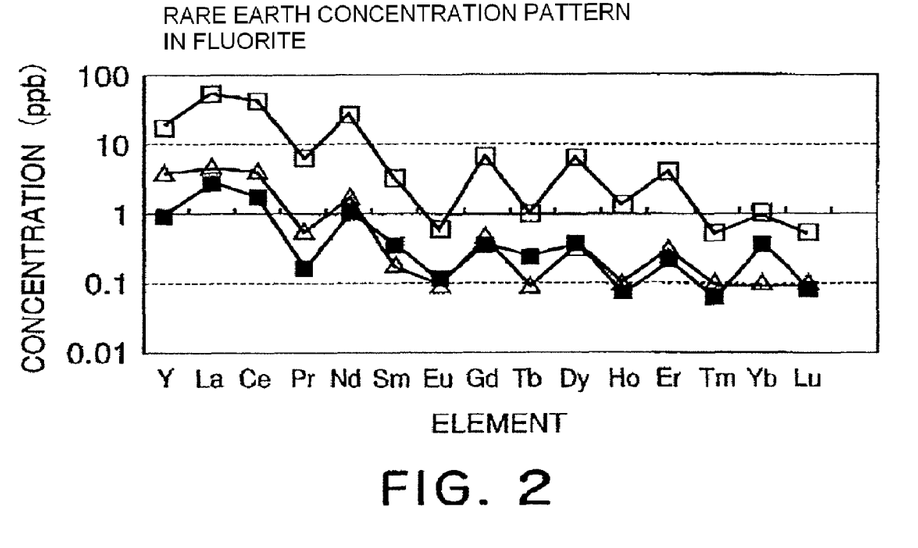
FIG. 2 is a graph for explaining a typical pattern of rare earth elements contained in fluorite.

Further, it has been confirmed that, for any fluorite sample having been assayed, there is a substantially constant rare-earth content pattern, such as shown in FIG. 2.

Generally, regardless of the types of elements, if fluorite contains impurities of an amount greater than a certain threshold, desired optical characteristics cannot be satisfied. Some elements have a greater influence upon the optical characteristics than do others, even if only a small amount of such elements is present. Those impurities that are currently regarded as problematic cannot be removed from a high-purity fluorite by any conventional means, which may influence optical characteristics. On the other hand, a question still remains as to whether impurities on a level of several tens ppb actually contribute to the deterioration of the optical characteristics. The inventor's findings, as described above, clearly indicate that the factor accounting for the deterioration of the optical characteristics of a high-purity fluorite, which has not been identified prior to the present invention, is a slight trace level of rare earth impurities, and not at all the crystalline structure of fluorite. Even the mixture pattern thereof has been specified. Indeed, these facts are groundbreaking and provide a prospect for future fluorite development. Further, the present invention provides an impurity assaying method, which is imperative to impurity reduction. Thus, the present invention provides a boost to the area of fluorite development.

In the specification, the rare earth element concentration may be referred to as 50 ppb or less, for example. From this content pattern, for ordinary fluorite, this can be accomplished if the concentration of Ce or the like is not greater than 50 ppb.

On the basis of the ground-breaking findings, as described above, the present invention provides an optical material, which is suitable for use with vacuum ultraviolet light, such as an $F_2$ excimer laser light, and which contains calcium fluoride as a main component, wherein the content of each rare earth element (Y, La, Ce, Pr, Nd, Sm, Eu, Gd, Tb, Dy, Ho, Er, Tm, Yb and Lu) is not greater than 50 ppb, respectively. Here, the value "50 ppb" is the level corresponding to the durability and transmissivity that satisfy the optical characteristics standard set by the inventor. Among these optical materials, those having a rare earth element content of not greater than 3 ppb can show extremely good durability and transmissivity, and they can be satisfactory as an optical material suitable for use with vacuum ultraviolet light.

The present invention provides an optical system, characterized by the use of such an optical material described above, which is suitable for use with vacuum ultraviolet light, such as an $F_2$ excimer laser light.

Also, the present invention provides an exposure apparatus, characterized by the use of an optical system described above as a semiconductor exposure apparatus using vacuum ultraviolet light, such as an $F_2$ excimer laser light.

Also, the present invention provides a device manufacturing method, characterized by use of an exposure apparatus, such as that described above in an exposure process, for a semiconductor device manufacture in which micro-processing based on vacuum ultraviolet light, such as an $F_2$ excimer laser light, is required.

Further, the present invention provides a method of producing a fluorite crystal with good optical characteristics, which can be used with vacuum ultraviolet light, such as an $F_2$ excimer laser light, the method comprising a first step of fusing a fluorite raw material to provide a refined product, a second step of fusing and re-crystallizing the refined product to provide an ingot, a third step of annealing the obtained ingot at a temperature not greater than a melting point, thereby improving crystallinity and providing an annealed product. A quantitative assay for to at least one of the fifteen elements (Y, La, Ce, Pr, Nd, Sm, Eu, Gd, Tb, Dy, Ho, Er, Tm, Yb and Lu) is carried out with respect to at least one of the fluorite raw material, the refined product, the ingot and the annealed product. Then, the first, second and third steps are controlled on the basis of the results of the assay.

The present invention provides a fluorite crystal producing method, wherein an average content of each of Y, La, Ce, Pr, Nd, Sm, Eu, Gd, Tb, Dy, Ho, Er, Tm, Yb and Lu is not greater than 100 ppb.

The present invention provides a fluorite crystal producing method, wherein an average content of each of Y, La, Ce, Pr, Nd, Sm, Eu, Gd, Tb, Dy, Ho, Er, Tm, Yb and Lu in the refined product is not greater than 80 ppb.

The present invention provides a fluorite crystal producing method, wherein an average content of each of Y, La, Ce, Pr, Nd, Sm, Eu, Gd, Tb, Dy, Ho, Er, Tm, Yb and Lu in the ingot is not greater than 50 ppb.

The present invention provides a fluorite crystal producing method, wherein an average content of each of Y, La, Ce, Pr, Nd, Sm, Eu, Gd, Tb, Dy, Ho, Er, Tm, Yb and Lu in the annealed product is not greater than 50 ppb.

With respect to the average content of rare earth elements in the refined product, ingot and annealed product, a sample was collected so that it is uniform with respect to the crystal growth direction, and the average content was represented by the concentration in that sample. A column-like shape is hollowed out along the growth direction.

This is due to the tendency of the impurities to increase further if solidification occurs at a later stage (recrystallization effect).

Further, the present invention provides a fluorite crystal producing method, characterized by the use of the ICP-MS assay method as a quantitative assay method, a fluorite crystal producing method, characterized by the use of any of the aforementioned assay methods as the quantitative assay method, and a fluorite crystal producing method, characterized by the use of the laser abrasion ICP-MS assay method.

Further, the present invention provides a fluorite as an optical material suitable for use with vacuum ultraviolet light, such as an $F_2$ excimer laser light, in which at least one of the aforementioned fluorite crystal producing methods is applied.

Further, the present invention provides an optical system suitable for a vacuum ultraviolet light, such as an $F_2$ excimer laser light, in which such fluorite is used.

Further, the present invention provides an exposure apparatus, as a semiconductor exposure apparatus using vacuum ultraviolet light, such as an $F_2$ excimer laser light, in which such an optical system is used.

Also, the present invention provides a device manufacturing method, characterized by the use of an exposure apparatus such as that described above in an exposure process for device manufacture, as a semiconductor device manufacture in which micro-processing based on vacuum ultraviolet light, such as an $F_2$ excimer laser light, is required.

Further, the present invention provides a method of evaluating optical characteristics of fluorite, characterized in that a quantitative assay is performed with respect to at least one rare earth element selected from Y, La, Ce, Pr, Nd, Sm, Eu, Gd, Tb, Dy, Ho, Er, Tm, Yb and Lu in the fluorite, to evaluate the durability and transmissivity of the fluorite crystal to ultraviolet light. The optical characteristics are predicted based on the impurity content.

The present invention provides optical characteristics evaluation method for fluorite, in which those having average weight rates of rare earth elements not greater than 50 ppb are considered to be superior fluorite crystals.

These and other objects, features and advantages of the present invention will become more apparent upon a consideration of the following description of the preferred embodiments of the present invention taken in conjunction with the accompanying drawings.

DESCRIPTION OF THE PREFERRED EMBODIMENTS

Preferred embodiments of the present invention are described below with reference to the drawings.

Figure 3:
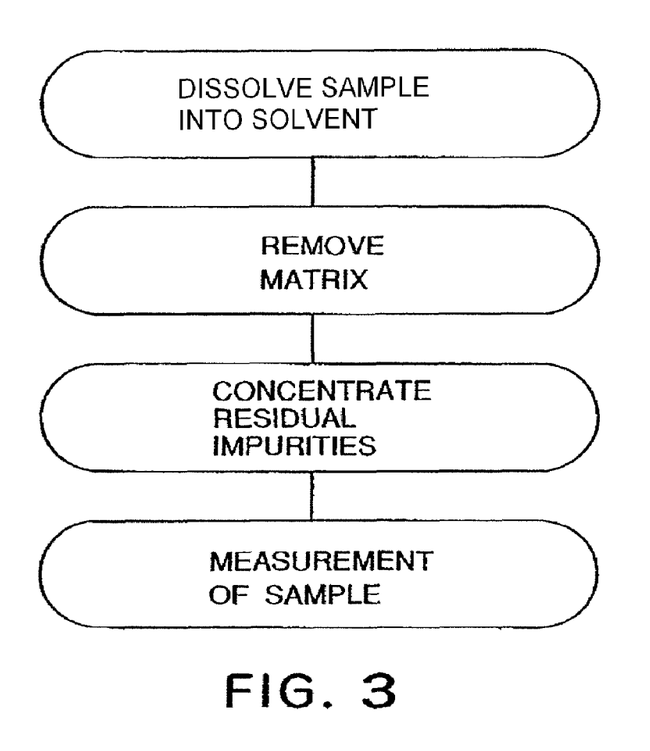
FIG. 3 is a flow chart of a fluorite assaying method according to an embodiment of the present invention.

Referring now to FIG. 3, an embodiment of a quantitative assay method for fluorite, which is several times more sensitive than conventional methods, will be described. In accordance with the assay method of this embodiment, the sample pre-processing method comprises processes of dissolution of a fluorite sample, removal of a matrix (such as Ca, F and solvent used for the dissolution), and concentration of contained impurity elements.

First, a sample to be measured is prepared. For a solid mass, a sample of an appropriate amount can be obtained, for example, by cleavage, cutting or breaking. A powder sample can be used as it is. After a sample is obtained, a solution is made. If, however, surface contamination is to be removed before the solution is made, the sample surface may be removed by fusing. For example, inside a clean closed container, which can be heated and which does not cause a reaction to occur, a sample may be immersed in a diluted hydrochloric acid or diluted nitric acid or, alternatively, concentrated sulfuric acid. After being closed, it may be heated. Similarly, inside a clean closed container, which can be heated and which does not cause a reaction to occur, a sample may be immersed in perchloric acid and then heated. The surface can be removed by fusing in this manner. The heating may be done to facilitate efficient fusing.

As regards the thus obtained sample, if it is a mass, it is crushed by using a milling tool, such as clean a gate mortar or alumina mortar. This is done to expedite the fusing. Since, however, mortar may cause contamination, the fusing process may be initiated with the sample left as it is. As regards the milling tool, it may be cleaned, for example, by being immersed in the same nitric acid for a long period of time. Then, only a portion of the sample to be powdered may be crushed, and thereafter, sample crushing may be initiated. The degree of crushing should be moderate to avoid contamination from the milling tool.

Subsequently, the sample is dissolved into a solution. The obtained powder (or mass) sample is put into a clean container, which can be heated and which does not cause a reaction to occur, and after adding a solvent for dissolving the fluorite, the sample is held at an appropriate temperature, whereby it is fused. Examples of solvents for fusing fluorite are hydrochloric acid, nitric acid, sulfuric acid, and perchloric acid. For example, a sample may be measured in a Teflon pressure-resistant container having been washed by nitric acid, and diluted nitric acid may be added thereto. After closing the container, it may be placed in a heating oven so that the fluorite can be fused.

The next step is the removal of the matrix. This can be done in various ways, such as, for example, separation by absorption, separation by coprecipitation, and evaporation removal of unwanted matter. Now, HF evaporation removal and separation by absorption through ion exchange of impurity elements in fluorite will be described as an example. Of course, impurity elements may be separated through coprecipitation, for example, with $Fe(OH)_2$.

As regards evaporation removal of HF, an obtained solution is evaporated, and product HF in the solution, as well as excess solution that did not react with fluorite, are removed. For example, in the case of the nitric acid solution, if it is kept at 200° C. using a hot plate to remove the solvent, HF and nitric acid are vaporized and deliquescent $Ca(NO_3)_2 \cdot 4H_2O$ remains.

The subsequent step is separation by absorption of impurity elements in fluorite by ion exchange. In this example, first, the residual sample is dissolved. Namely, the aforementioned $Ca(NO_3)_2 \cdot 4H_2O$ is melted by diluted nitric acid.

The thus obtained solution is passed through a clean ion exchanging resin under an appropriate pH, whereby elements in question are absorbed. For example, an imino diacetate-type chelating resin refined and washed by diluted nitric acid may be put into a column. Then, and nitric acid, ammonium acetate aqueous solution and pH-adjusted sample solution may be passed through the resin in this order, whereby metal elements or rare earth ions may be absorbed to the resin. Subsequently, for washing and removing residual solution inside the column, ammonium acetate aqueous solution and ultra pure water may be passed therethrough. Finally, by using nitric acid, metal elements and rare earth ions absorbed by the resin may be extracted.

With the operations described above, the matrix, that is, Ca, F and a solvent used for the dissolution, can be removed. Further, in this example, the amount of nitric acid for extracting impurity elements absorbed by the resin can be maintained at a relatively low level, such that the concentration of impurities can be maintained at a much higher level (concentration process) than in fluorite solutions conventionally introduced to ICP-MS.

With the operations described above, a high-concentration fluorite solution, with Ca and HF removed considerably to be suitable for an ICP-MS measurement, can be provided. As compared with a 0.1% fluorite solution, which has been the upper limit to be introduced to ISP-MS because of the limitations imposed by the conventional Ca concentration, the solution now provided can lead to a high-impurity concentration that is one hundred times greater. Also, as a result, the detection limit for impurities in fluorite is improved such that it is a hundred times greater than was previously possible. Specifically, in the example described above, a limit of quantitative determination of 0.1 ppb was accomplished.

The content of impurities in fluorite was measured in accordance with the assay method of the present invention, with the content being as low as 0.1 ppb, and the correlation between the impurity content and the durability and transmissivity of fluorite was investigated in greater detail. As a result, it has been experimentally confirmed that there is a correlation between the rare earth element content and optical characteristics of fluorite, such as depicted in FIGS. 1A and 1B.

Additionally, it has been found that in every fluorite sample assayed, there is an approximately constant pattern for rare earth content, such as shown in FIG. 2.

An embodiment of the present invention for an optical material suitable for use with vacuum ultraviolet light, such as an $F_2$ excimer laser light, will be described. The optical material of the present invention comprises a fluorite optical material, which contains calcium fluoride as a major component, wherein rare earth elements, which contribute to deterioration of the optical characteristics, are present only in very small amounts, which do not influence the optical characteristics. This is based on the inventor's groundbreaking finding of the correlation between the impurity content and the optical characteristics.

Fluorite crystals having been produced as an optical material for vacuum ultraviolet light and having an average concentration of rare earth elements (Y, La, Ce, Pr, Nd, Sm, Eu, Gd, Tb, Dy, Ho, Er, Tm, Yb and Lu) that is not greater than 50 ppb were chosen arbitrarily, and their optical characteristics were evaluated. All the results followed the detected correlation, and it was confirmed that required optical characteristics were satisfied.

Figure 4:
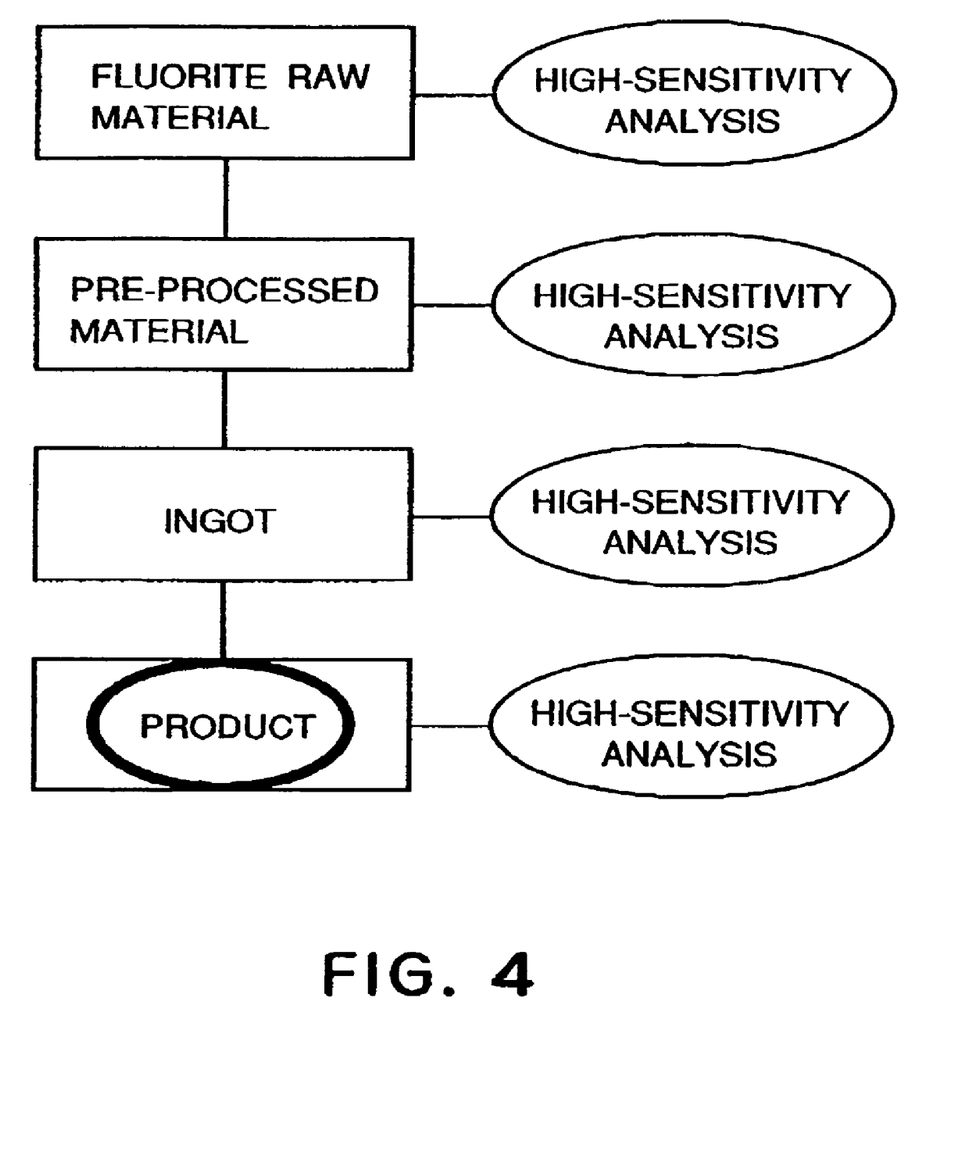
FIG. 4 is a flow chart for explaining fluorite crystal manufacturing processes.

An embodiment of a producing method for efficiently providing a fluorite crystal having superior optical characteristics will now be described with reference to FIG. 4. In the producing method according to the present invention, an assay of the rare earth element concentration is carried out at least at one stage in the manufacturing processes, and the process control is carried out on the basis of the results of the measurement. In an example of the producing method described below, the assay was carried out at each stage.

Regarding the production raw material for the fluorite crystal, usually, synthetic powder raw material having fewer impurities is used. First, for example, a rare earth assay of this raw material is performed in accordance with the assaying method of the present invention. On the basis of this assay, the composition of the material is controlled so that the rare earth content included in an annealed product that is produced is small. The inventor investigated the quantitative limits of the rare earth element content, which could be acceptable in the fluorite raw material for practical processes, and experimentally found that it should desirably be not greater than 100 ppb. It should be noted that, in fluorite, those portions solidified initially include fewer impurities, and portions solidified later include more impurities (recrystallization effect). Therefore, it is possible to reduce the rare earth content to some extent in the manufacturing processes. If the rare earth element content in the raw material is too high, the rare earth content in an annealed product is also too high, which prevents the formation of an optical element with superior optical characteristics.

The production process for a refined product will now be described. In this process, the fluorite raw material described above is fused and solidified together with a scavenger. A specific example is described below.

As a scavenger, a 0.1 mass % of $ZnF_2$ is added to a synthetic fluorite raw material, and then they are well mixed. The obtained mixture is placed into a clean container made, for example, of black lead, and then the mixture is heated in a vacuum atmosphere. After the mixture is fused, it is cooled slowly and solidified. Thereafter, the portion solidified later in time, and thus having more impurities, is removed. For example, where slow cooling is carried out in accordance with the Bridgeman method, the upper portion of the crystal may be removed.

With regard to the thus obtained refined product, a rare earth assay according to the assaying method of the present invention is carried out, and the process control is performed so that an annealed product obtained contains a very small concentration of rare earth elements. The inventor investigated the quantitative limits of the rare earth content in the refined product required for obtaining an annealed product having good optical characteristics, and experimentally found through practical processes that the average rare earth content in the refined product should desirably be not greater than 80 ppb.

A process for producing an ingot is described below. In this process, the above-described refined product is fused and solidified together with a scavenger. However, as compared with the refined product, it is cooled more slowly. This assures a good crystal having high crystallinity and a small grain boundary. A specific example is described below.

As a scavenger, a 0.01 mass % of $ZnF_2$ is uniformly spread over the refined product obtained as described. Then, it is put into a clean container made of black lead, for example, and it is heated in a vacuum atmosphere. After the mixture is fused, it is cooled and solidified by the Bridgeman method more slowly as compared with the refined product. Thereafter, the portion solidified later in time, and thus having more impurities contained therein, is removed. In this example, the upper portion of the crystal may be removed. With regard to the thus obtained ingot, a rare earth assay according to the assaying method of the present invention, for example, is carried out, and the process control is performed so that the final annealed product to be obtained has a lower rare earth content. The inventor investigated the quantitative limit of the rare earth elements that can be present in the ingot and still result in the annealed product having good optical characteristics, and experimentally found that the average rare earth content in the ingot should desirably be not greater than 50 ppb.

Finally, a production process for the annealed product will be described. In this process, the above-described ingot is kept at a temperature not higher than a melting point thereof, and, thereafter, it is cooled slowly at a speed equivalent to or slower than that in the ingot production. Through this thermal treatment, residual stress due to the distortion produced inside the ingot can be reduced, such that birefringence therein can be reduced. A specific example is described below.

The ingot obtained as described is put into a clean container made, for example, of back lead. At this time, $ZnF_2$ may be added as a scavenger. With respect to the atmosphere, a vacuum atmosphere or an inert gas atmosphere, for example, is preferable. In this state, heating is carried out at a temperature not greater than the melting point. After the ingot is held at an elevated temperature for a predetermined time period, it is cooled slowly within a temperature range sensitive to crystal structure formation, at a speed equivalent to or slower than that during the ingot production.

With regard to the thus obtained annealed product, a rare earth assay according to the assaying method of the present invention, for example, is carried out, so as to directly control the rare earth content included in the final product. The inventor investigated the quantitative limit of the rare earth elements that can be present in the annealed product and still lead to good optical characteristics, and experimentally found through practical processes that the average rare earth content in the annealed product should desirably be not greater than 50 ppb.

As regards the average content of rare earth elements in the refined product, ingot and annealed product, a sample, which is uniform with respect to the crystal growth direction, was collected, and the average content was represented by the concentration in that sample. This may be achieved, for example, by hollowing out a column-like shape along the crystal growth direction. This is due to the tendency of the impurity content to increase later in time during the solidification process (recrystallization effect).

An embodiment of a unique optical characteristics evaluation method for fluorite of the present invention, which is based on the groundbreaking finding as discussed above, is described below. One of the features of the optical characteristics evaluation method of the present invention is that the optical characteristics can be predicted on the basis of assaying the rare earth content in a fluorite crystal.

First, plural fluorite crystals manufactured for use with an ArF or $F_2$ excimer laser were prepared arbitrarily. Then, the average contents of rare earth elements in them were measured by use of an assay method according to the present invention. As regards the sample collection, in order for the sample to be uniform with respect to the fluorite crystal growth direction, the fluorite was cut along a plane parallel to the growth direction, and an average concentration thereof was measured.

On the basis of the results of the assay of the rare earth concentration, the prepared fluorite crystals were classified into a group in which the rare earth content is not greater than 50 ppb and a group in which the content of at least one rare earth element is more than 50 ppb. Then, by using vacuum ultraviolet light, the durability and transmissivity were actually evaluated. The result is that, in the group in which the content of each rare earth element is less than 50 ppb, the prescribed optical characteristics were satisfactory. In the other group, in which at least one rare earth element was present at a concentration of more than 50 ppb, the prescribed optical characteristics were not satisfied. It should be noted that the rare earth concentration and the optical characteristics satisfied the correlation found by the inventor. As described above, by measuring the rare earth concentration in the fluorite crystal, the optical characteristics of fluorite can be very accurately evaluated.

Embodiments of an optical system and an exposure apparatus using fluorite, as well as a device manufacturing method using such an exposure apparatus, are described below.

A fluorite produced in accordance with the present invention has good durability and high transmissivity with respect to vacuum ultraviolet light, such as an $F_2$ excimer laser light. For this reason, where an optical system is manufactured using such fluorite, a satisfactory optical system, in which light absorption or decrease in transmissivity to ultraviolet light is as desired and which is stable in illuminance, can be provided.

Further, when such an optical system is incorporated into a semiconductor exposure apparatus, a semiconductor exposure apparatus with a very small decrease in illuminance, which assures good productivity, can be provided.

Further, since the deterioration of the imaging performance due to the aberration by thermal expansion is small, the use of a semiconductor exposure apparatus such as that described above, can provide a stable device manufacturing method.

Now, specific examples of the present invention will be described in detail.

EXAMPLE 1

Example 1 relates to an assaying method for fluorite, with sensitivity several times greater than in conventional methods.

First, a 3 g fluorite sample to be assayed for impurities was collected as a mass by cleavage. Since the surface of this sample was contaminated, the assay was not initiated directly. The sample was immersed in a Teflon beaker with perchloric acid. It was heated at about 200° C. for about 20 minutes, whereby the surface was fused and removed. The operation was carried out twice.

The mass sample, having had its surface fused and removed, was washed by ultra pure water and, by using a Teflon evaporation plate, it was immersed in 15 ml of perchloric acid. Then, the sample was heated on a hot plate at 180° C. until it was dried and solidified. With that procedure, produced HF in the solution, as well as excess acid that had not reacted with fluorite, were removed. To avoid contamination, it was heated in a clean booth. For a similar reason, in this example, the sample powdering was not carried out.

The thus obtained material was dissolved by 3.4% diluted nitric acid. At that time, there was a residual fluorite sample that was not melted. Thus, perchloric acid of an appropriate amount was added, and similar heating fusion and dissolution were carried out. Through these operations, a diluted nitric acid solution in which a 3 g fluorite sample was dissolved was obtained. Then, the pH was adjusted to 6 by using ammonia water, and subsequently, the solution was separated into two separate solutions.

The volume of each of these two solutions was 100 ml. Rare earth elements (the subject of the assay) were added to only one of these solutions by an amount corresponding to 3 ppt in terms of the concentration in solution.

The thus obtained two solutions were passed through imino diacetate-type chelating resins, respectively, at a speed of 1 ml/min, whereby metal elements and rare earth elements, etc., were separated by absorption. The chelating resin was pre-processed as follows. First, for refining, a resin of 50 ml was put into a beaker and, together with 100 ml of 2N nitric acid, it was left for four or five hours while being gradually stirred. Thereafter, it was washed several times by ultra pure water. This operation was repeated once, and then, 2 ml of the resin was placed into a Teflon column. Then, 8 ml of 2N nitric acid, 8 ml of 0.1N nitric acid and 8 ml of 0.2N ammonium acetate aqueous solution (pH=6) were passed therethrough.

After the sample passed through the resin, again, 5 ml of 0.2M ammonium acetate aqueous solution (pH=6) and 5 ml of ultra pure water were passed through it. Finally, 10 ml of 1N nitric acid was passed through the resin, whereby rare earth elements and metal elements absorbed by the resin were extracted. Further, by using ultra pure water, the volume of the elements-extracted solution was adjusted to 20 ml. These solution-making operations were carried out with respect to each of the two solutions. Through the described procedure, elements, such as Al, V, Ni, Co, Cu, Au, Ga, Ag, Cd, Pb, U, Y, La, Ce, Pr, Nd, Sm, Du, Gd, Tb, Dy, Ho, Er, Tm, Yb and Lu, can be effectively separated from Ca ions.

With the operations described above, on the basis of a 3 g fluorite sample, two high-concentration fluorite solutions (20 ml), having a considerably reduced Ca—HF amount and being suitable for an ICP-MS measurement, can be produced.

By using these two solutions, a quantitative measurement based on ICP-MS was carried out. On the basis of the information regarding the difference in concentration between the two solutions, the recovery rate for rare earth elements through the chelating concentration was calculated. Namely, if the recovery rate is 100%, the concentration difference of solutions to be measured would be 15 ppt. If, on the other hand, the recovery rate is 50%, the concentration difference would be 7.5 ppt. The recovery rate for the rare earth elements according to the procedure of this example was about 80-100%. By using the assaying method as described above, a limit of quantitative determination of 0.1 ppb was obtained for rare earth elements with respect to a fluorite sample.

EXAMPLE 2

Example 2 concerns an optical material suitably usable with vacuum ultraviolet light, such as an $F_2$ excimer laser light.

From a disk-like annealed product, which was produced as a fluorite lens material for the ArF stepper, a cylindrical test piece of 30φ from an edge of the annealed product was cut. The side face of the test piece was cut, and the average rare earth concentrations in the obtained fragments were measured. ArF transmissivity and durability of the fragments with a rare earth concentration of not greater than 50 ppb were investigated, and the result was that all fragments showed good optical characteristics and satisfied the prescribed standards. The transmissivity and durability conformed with the correlation with the rare earth concentration found by the inventor.

EXAMPLE 3

Example 3 concerns a method of producing a fluorite crystal suitable for use with vacuum ultraviolet light, such as an $F_2$ excimer laser light.

First, the rare earth concentration in synthetic calcium fluoride powder, i.e., the raw material of fluorite crystal, was measured in accordance with the method used in Example 1. The result was that the rare earth concentration was approximately registered with a rare earth pattern, and the Y concentration, as a representative value, was 67 ppb. Further, the concentrations of the other rare earth elements were not greater than 75 ppb. Thus, only raw materials having a rare earth concentration not greater than 100 ppb were selected, and they were used in the subsequent production.

Then, a refined product was produced, and the rare earth concentration of that sample was assayed in accordance with the method used in Example 1. The refined product was made as follows.

0.1 mass % of $ZnF_2$ powder was added to a calcium fluoride powder material, and they were well mixed. The mixture was put into a clean container made of black lead, and the container was put into a heating device arranged for vacuum evacuation. While maintaining a vacuum of about $10^{-6}$ torr inside the heating device, the container was heated up to 1450° C. After that, it was cooled by the Bridgeman method to room temperature. Then, the top surface portion, where there were relatively more impurities, was removed by about 10% in volume ratio. With this procedure, a refined product (i.e., polycrystalline fluorite) was obtained.

Then, a sample that is uniform with respect to the crystal growth direction was assayed. As a result of the assay, it was confirmed that the rare earth concentration was substantially in conformity with a rare earth pattern, and the Y concentration, as a representative value, was 53 ppb. The concentrations of the other rare earth elements were not greater than 59 ppb.

As described, only those refined products having a rare earth concentration not greater than 80 ppb were selected, and they were used in the subsequent production.

Then, an ingot was produced, and the rare earth concentration of the sample was assayed in accordance with the method used in Example 1. The ingot was produced as follows.

As a scavenger, $ZnF_2$ of 0.01 mass % was sprinkled over the refined product, produced as described above. Then, it was put into a clean container made of black lead, and the container was put into a heating device arranged for vacuum evacuation. While maintaining the vacuum at about $10^{-6}$ torr inside the heating device, the container was heated up to 1450° C. After that, it was cooled by the Bridgeman method to room temperature. Then, the top surface portion, where there were relatively more impurities, was removed by about 10% in volume ratio. With this procedure, an ingot was obtained.

A sample of the ingot with a uniform growth direction was essayed. As a result of the assay, it was confirmed that the rare earth concentration was substantially in conformity with a rare earth pattern, and the Y concentration, as a representative value, was 28 ppb. The concentrations of the other rare earth elements were not greater than 32 ppb. As described, only those ingots having a rare earth concentration not greater than 50 ppb were selected, and they were used in the subsequent production.

Then, an annealed product was produced, and the rare earth concentration of the sample was assayed in accordance with the method used in Example 1. The annealed product was produced as follows.

The ingot obtained as described above was processed into a predetermined shape, and the thus shaped product was put into a clean container made of black lead. Then, it was put into a heating device arranged for vacuum evacuation. The container was heated up to 1000° C. within a vacuum of a level of about 10 torr, and it was held for 20 hours. After that, it was cooled slowly to 600° C. at a speed of 0.7° C./h. Thereafter, it was cooled to room temperature, whereby an annealed product was obtained.

The sampling of the annealed product was made, so that the portion to be ground in the final polishing step was cut along a plane parallel to the crystal growth direction, so as to facilitate the determination of the average concentration of the annealed product. As a result of the assay, it was confirmed that the rare earth concentration was substantially in conformity with a rare earth pattern, and the Y concentration, as a representative value, was 28 ppb. The concentrations of the other rare earth elements were not greater than 32 ppb. As described, only those annealed products having a rare earth concentration not greater than 50 ppb were selected as successful products, and they were used in the subsequent production.

The durability and transmissivity of the annealed products thus obtained were measured, and it was confirmed that they were superior fluorite crystals satisfying the prescribed standards.

EXAMPLE 4

Example 4 concerns an optical characteristic evaluation method for a fluorite crystal suitable for use with vacuum ultraviolet light, such as an $F_2$ excimer laser light.

First, plural fluorite crystals, which were manufactured for use with an ArF or $F_2$ excimer laser, were prepared arbitrarily. Then, the average contents of rare earth elements in these crystals were measured by use of an assay method according to the present invention. As regards the measurement sample collection, the fluorite was cut along a plane parallel to the fluorite crystal growth direction, and an average concentration thereof was measured.

On the basis of the results of the assay of the rare earth concentration, the prepared fluorite crystals were classified into a group in which the rare earth content is not greater than 50 ppb and a group in which the content of at least one rare earth element is more than 50 ppb. That is, the former is a group of materials with good optical characteristics, while the latter is a group that does not have good optical characteristics. Then, in order to confirm that this classification was valid, the durability and transmissivity of the materials were evaluated by using vacuum ultraviolet light. As a result, it was shown that in the group in which each rare earth material was present at a concentration of less than 50 ppb, the prescribed optical characteristics were confirmed. In the other group in which at least one rare earth element was present at a concentration of more than 50 ppb, the prescribed optical characteristics were not satisfied. It should be noted that the rare earth concentration and the optical characteristics satisfied the correlation found by the inventor. As described above, by measuring the rare earth concentration in the fluorite crystal, the optical characteristics of fluorite can be very accurately evaluated.

EXAMPLE 5

Example 5 concerns an optical system using an optical material suitable for use with vacuum ultraviolet light, such as an $F_2$ excimer laser light, a semiconductor manufacturing exposure apparatus, and a device manufacturing method using such an exposure apparatus.

Figure 5:
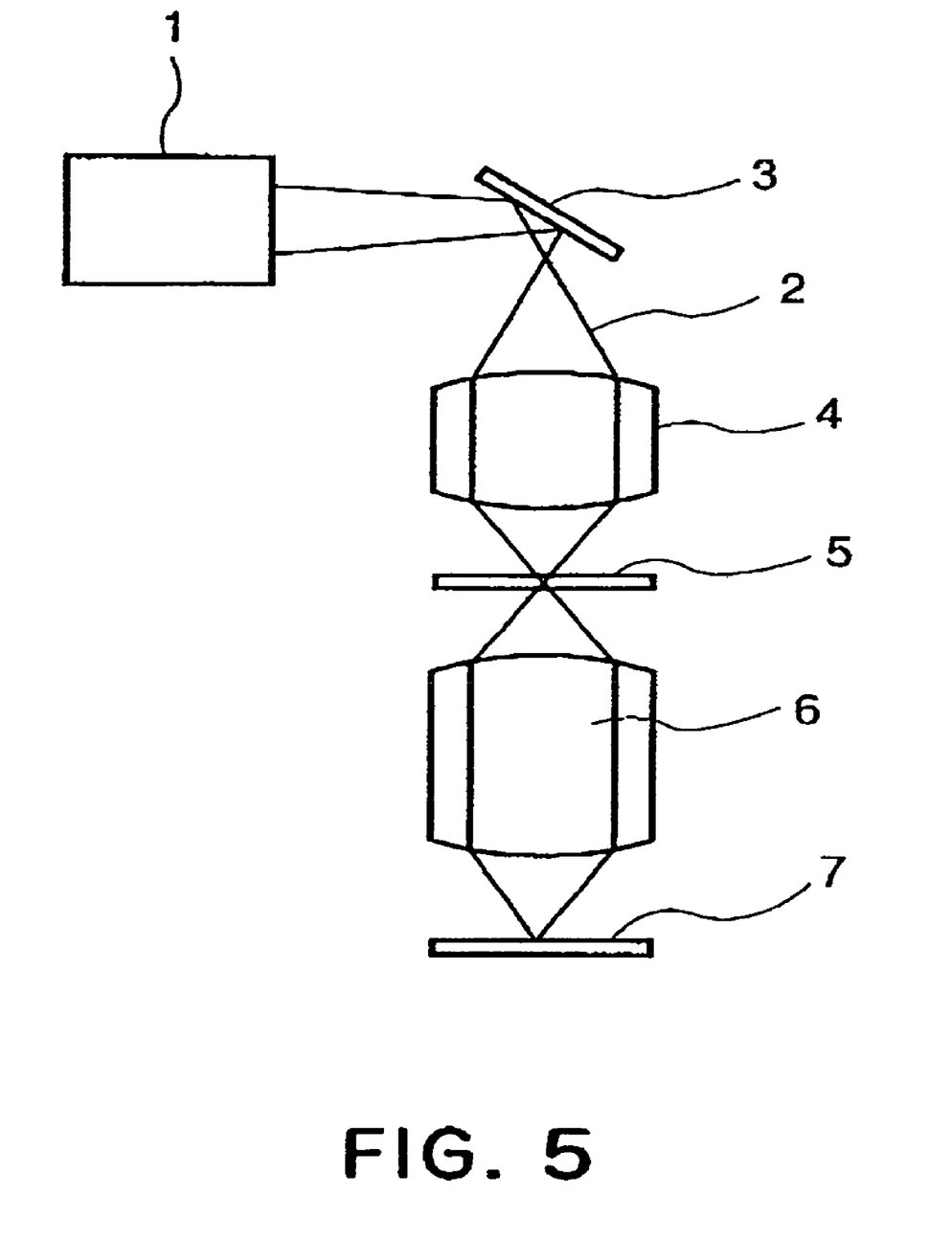
FIG. 5 is a schematic view of a semiconductor manufacturing exposure apparatus according to an embodiment of the present invention.

FIG. 5 is a schematic view of a semiconductor manufacturing exposure apparatus.

Denoted as reference numeral 1 in the drawing is a light source, which, in this Example, comprises an ArF excimer laser. Light beam 2 emitted from the light source 1 is directed by a mirror 3 toward an illumination optical system 4. The light beam passing through the illumination optical system 4 illuminates a surface of the reticle 5 (first object) The light passing through the reticle 5 and bearing information about the reticle goes through a reduction projection optical system 6, whereby it is projected on a photosensitive substrate 7.

The illumination optical system and/or the projection optical system of the semiconductor exposure apparatus of this example uses fluorite as well as quartz. The fluorite used here is one identified as a good article in Example 2, manufactured in Example 3, or identified as good in Example 4.

It should be noted that, in this Example, all the lenses included in the illumination optical system 4 and the reduction projection optical system 6 and made of fluorite contain calcium fluoride as a major component, and the content of the fifteen elements (Y, La, Ce, Pr, Nd, Sm, Eu, Gd, Tb, Dy, Ho, Er, Tm, Yb and Lu) is not greater than 3 ppb.

A semiconductor manufacturing exposure apparatus according to Example 5 was used for one year to carry out normal operations. The illuminance on the reticle surface, after such use, was measured. The result is that the illuminance was approximately at the same level as that before the apparatus was used. Further, the illuminance on the photosensitive substrate surface (wafer surface) was measured and found to be substantially at the same level as that measured before the apparatus was used.

As described above, a fluorite according to the present invention has a good durability and superior transmissivity with respect to ArF excimer laser light, such that, even after an exposure apparatus is used for a long time, sufficient transmissivity is assured. Additionally, aberration by thermal expansion is small. Thus, for an illumination optical system, a decrease in illuminance is small and, for a projection optical system, the imaging stability is high. In summary, an exposure apparatus that is superior in throughput and quality stability can be provided.

Next, an embodiment of a device manufacturing method, which uses an exposure apparatus described above, will be explained.

Figure 6:
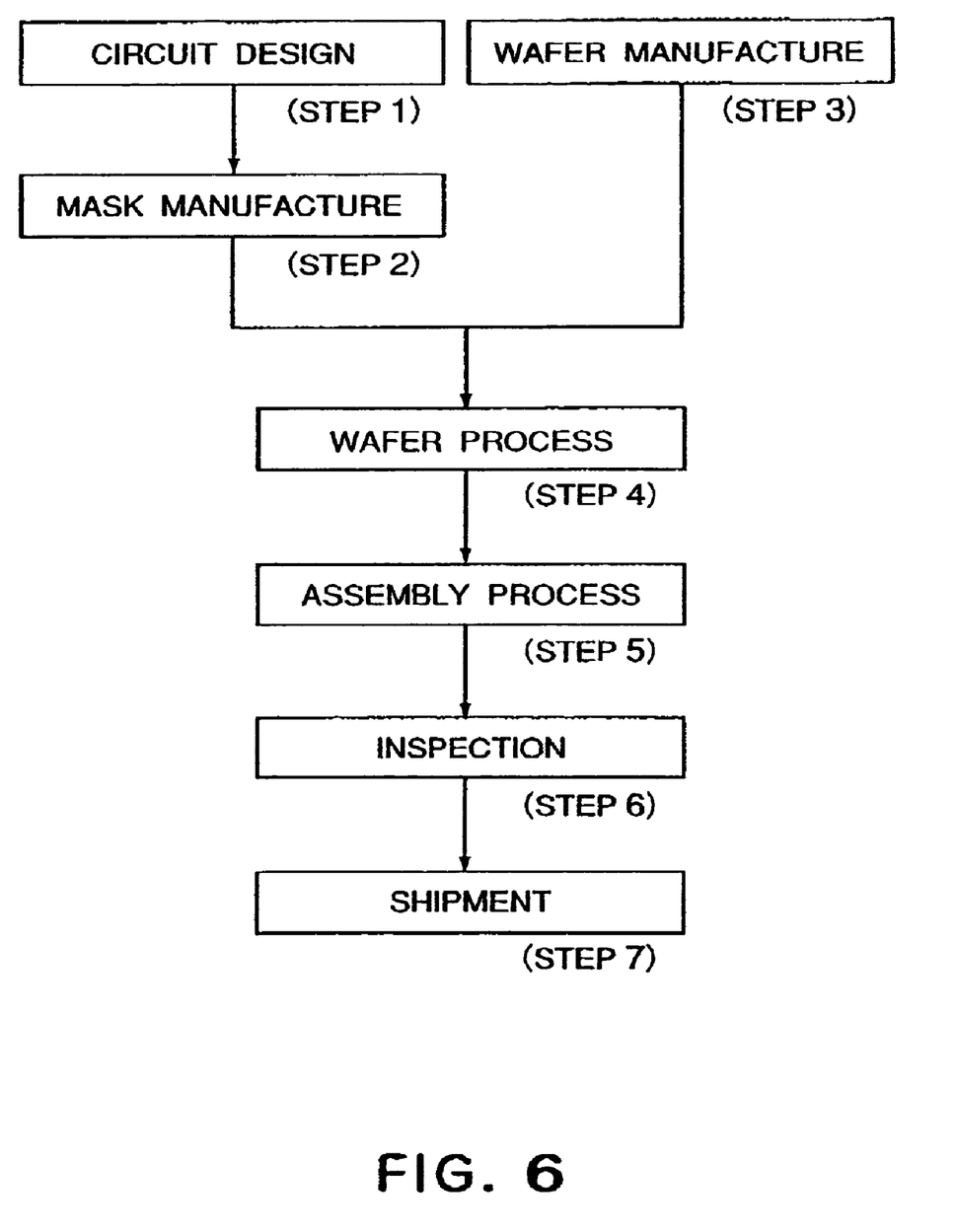
FIG. 6 is a flow chart for explaining semiconductor device manufacturing processes.

FIG. 6 is a flow chart for explaining the procedure of manufacturing various microdevices, such as semiconductor chips (e.g., ICs or LSIs), liquid crystal panels, CCDs, thin film magnetic heads or micro-machines, for example. Step 1 is a design process for designing a circuit of a semiconductor device. Step 2 is a process for making a mask on the basis of the circuit pattern design. Step 3 is a process for preparing a wafer by using a material, such as silicon. Step 4 is a wafer process in which, by using the thus prepared mask and wafer, a circuit is formed on the wafer in practice, by a lithographic method. Subsequent step 5 is an assembling step in which the wafer processed in step 4 is formed into semiconductor chips. This step includes an assembling (dicing and bonding) process and a packaging (chip sealing) process. Step 6 is an inspection step, wherein an operation check, a durability check, and so on, are carried out for the semiconductor devices produced by step 5. With these processes, semiconductor devices are produced and shipped (step 7).

Figure 7:
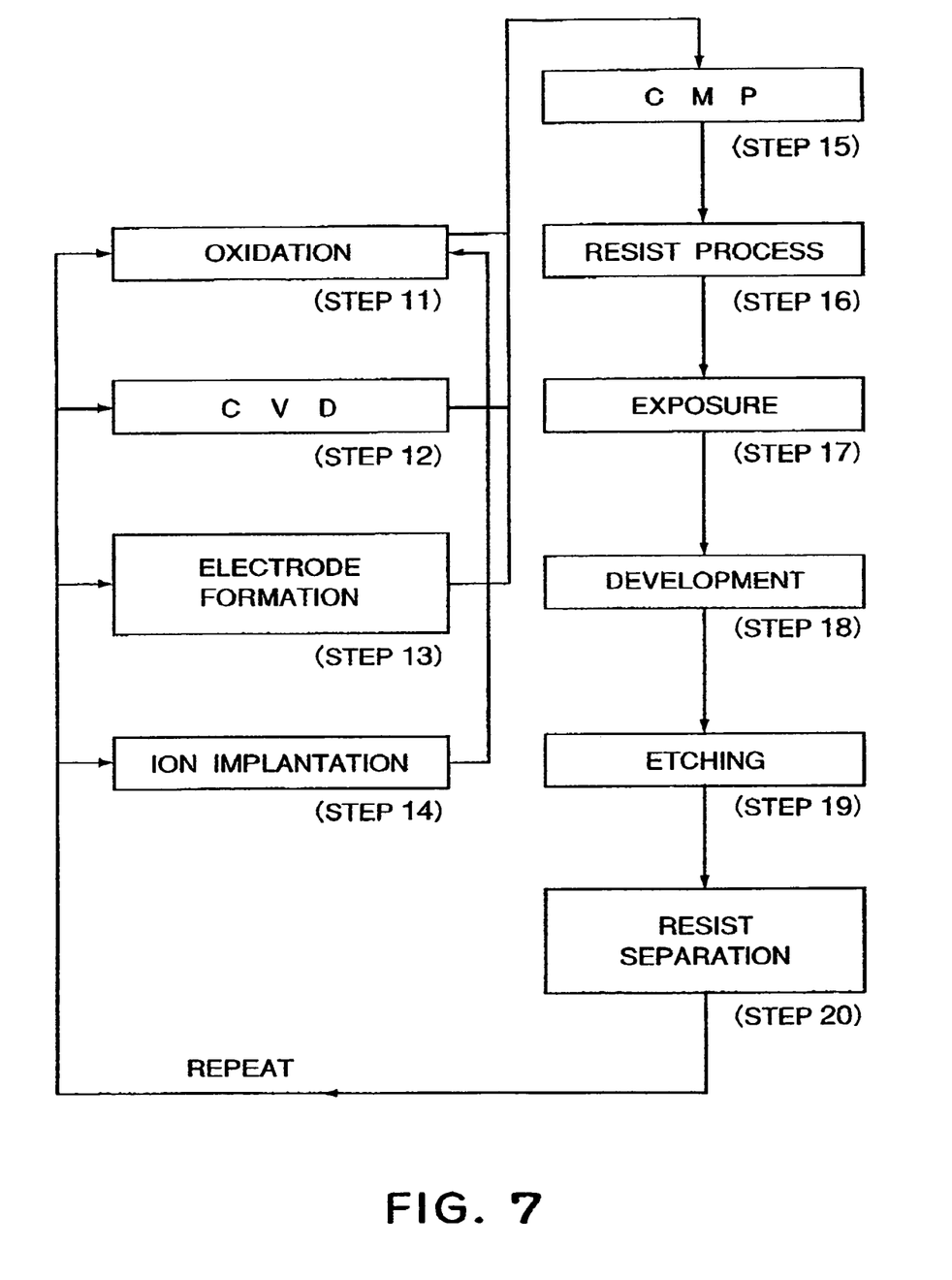
FIG. 7 is a flow chart for explaining details of a wafer process, including that in the procedure of FIG. 6.

FIG. 7 is a flow chart for explaining the details of the wafer process. Step 11 is an oxidation process for oxidizing the surface of a wafer.

Step 12 is a CVD process for forming an insulating film on the wafer surface. Step 13 is an electrode forming process for forming electrodes upon the wafer by vapor deposition. Step 14 is an ion implanting process for implanting ions in the wafer. Step 15 is a chemical mechanical polishing step (CMP process) for polishing the wafer surface so that it is flat by a CMP device. Step 16 is a resist process for applying a resist (photosensitive material) to the wafer that has been flattened. Step 17 is an exposure process for printing, by exposure, the circuit pattern of the mask on the wafer through the exposure apparatus described above. More specifically, a reticle is conveyed and it is chucked by a reticle chuck. Then, a wafer substrate coated with a resist is loaded into the exposure apparatus. At an alignment station, data for global alignment is read out, and on the basis of the measurement results, the wafer stage is moved so that exposures are carried out successively at predetermined positions. Step 18 is a developing process for developing the exposed wafer. Step 19 is an etching process for removing portions other than the developed resist image. Step 20 is a resist separation process for separating the resist material remaining on the wafer after being subjected to the etching process. By repeating these processes, circuit patterns are formed on the wafer in a superimposed manner.

With these processes, high-density microdevices can be manufactured stably and at a decreased cost.

In accordance with the present invention, impurities, such as metal elements or rare earth elements, which could not be detected by conventional methods, despite influencing the durability or decreasing transmissivity, can be detected with a good precision. Consequently, the correlation between the impurities and optical characteristics is identified, such that fluorite having good optical characteristics, a method of effectively producing such fluorite, an evaluation method for optical characteristics, for example, can be provided.

While the invention has been described with reference to the structures disclosed herein, it is not limited to the details set forth above, and this application is intended to cover such modifications or changes as may come within the purposes of the improvements or the scope of the following claims.

What is claimed is:

1. A method of producing a fluorite crystal comprising:
    a first step of fusing a fluorite raw material to provide a preconditioned material;
    a second step of fusing and crystallizing the preconditioned material to provide an ingot;
    a third step of annealing the ingot at a temperature not greater than a melting point to improve crystallinity thereof and provide a product; and
    a quantitative assay step of carrying out a quantitative assay of a fluorite sample of at least one of the fluorite raw material, the preconditioned material, the ingot, and the product for at least one element selected from the group consisting of Y, La, Ce, Pr, Nd, Sm, Eu, Gd, Tb, Dy, Ho, Er, Tin, Yb, and Lu,
    wherein the quantitative assay is carried out before and/or after at least one of the first, second and third steps such that the at least one of the first, second, and third steps is controlled based on a result of the quantitative assay, wherein a pre-processing step is carried out before the quantitative assay, and wherein the pre-processing step comprises:

dissolving the fluorite sample by nitric acid into a calcium nitrate solution;

obtaining a solidified calcium nitrate by heating and drying the calcium nitrate solution and removing HF and nitric acid produced in the calcium nitrate solution, separating the at least one element by absorption by dissolving the solidified calcium nitrate into an aqueous solution and passing the aqueous solution through an imino diacetate chelating resin; and concentrating the at least one element by extraction from the resin using nitric acid and removal of Ca, F, and nitric acid.

* * * * *